United States Patent [19]

Toye

[11] Patent Number: 4,471,778

[45] Date of Patent: Sep. 18, 1984

[54] APPARATUS AND METHOD FOR PROVIDING OPENING INTO BODY CAVITY OR VISCUS

[76] Inventor: Frederic J. Toye, 1760 Termino Ave., Ste. 214, Long Beach, Calif. 90804

[21] Appl. No.: 409,960

[22] Filed: Aug. 20, 1982

Related U.S. Application Data

[63] Continuation-in-part of Ser. No. 206,709, Nov. 14, 1980, Pat. No. 4,364,391.

[51] Int. Cl.³ .................... A61M 5/00; A61F 17/32
[52] U.S. Cl. .......................... 128/305.3; 128/341; 604/160; 604/166
[58] Field of Search ............... 128/305.3, 341, 200.26, 128/207.15; 604/158, 160, 161, 164, 166

[56] References Cited

U.S. PATENT DOCUMENTS

| | | | |
|---|---|---|---|
| 3,225,762 | 12/1965 | Guttman | 604/164 |
| 3,384,087 | 5/1968 | Brummelkamp | 128/305.3 |
| 3,511,243 | 5/1970 | Toy | 128/305.3 |
| 3,651,807 | 3/1972 | Huggins | 604/161 |

Primary Examiner—Stephen C. Pellegrino
Attorney, Agent, or Firm—Fulwider, Patton, Rieber, Lee & Utecht

[57] ABSTRACT

An apparatus and method for providing a percutaneous or non-dissection opening into a body cavity or hollow viscus. A needle is attached to a syringe for insertion within the body cavity. Operation of the syringe confirms proper location of the needle within the body cavity. The needle is structurally weakened along a longitudinal line and includes elements operable to split the needle along the line to provide a longitudinal slot. An elongated dilator slidably fits through a side opening in a flexible tube and extends through the distal end of the tube. A leader attached to the distal end of the dilator is adapted for insertion through the bore of the needle, the slot in the needle enabling lateral separation of the leader for removal of the needle from the body cavity. The dilator is adapted to be forceably inserted into the body cavity along the path defined by the leader, and is thereafter removable through the side opening in the tube. The tube is thereafter further insertable into the body cavity.

7 Claims, 17 Drawing Figures

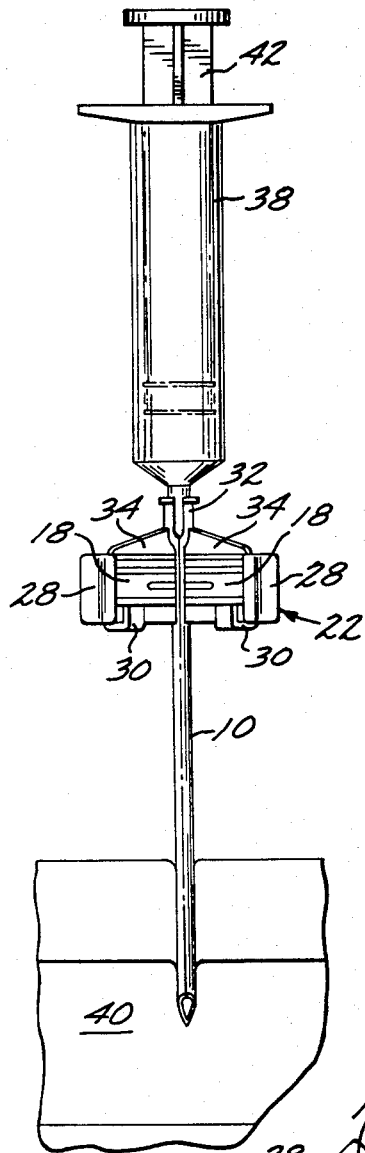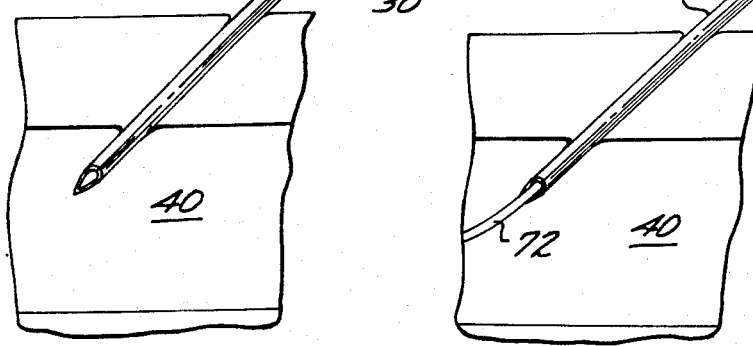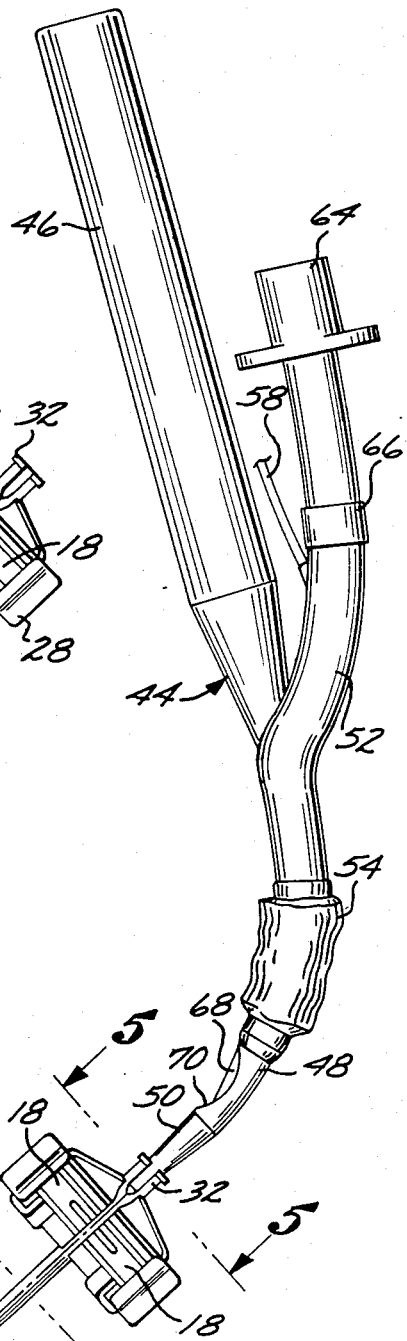

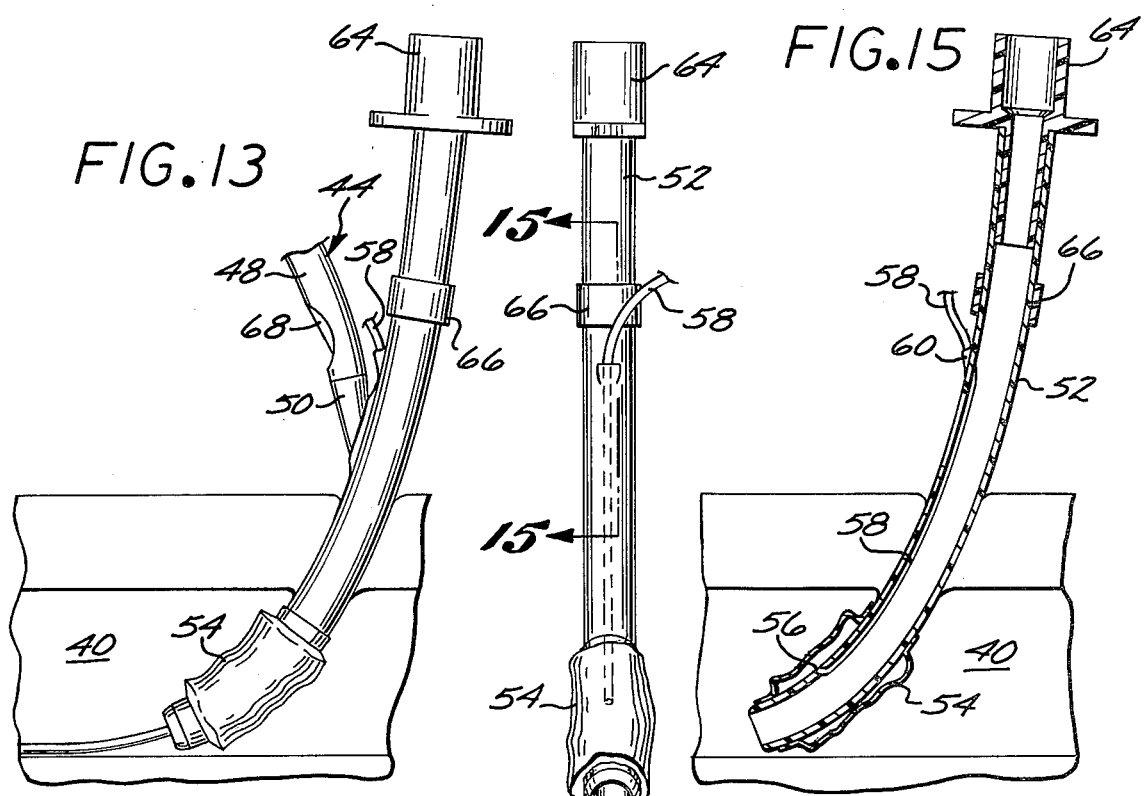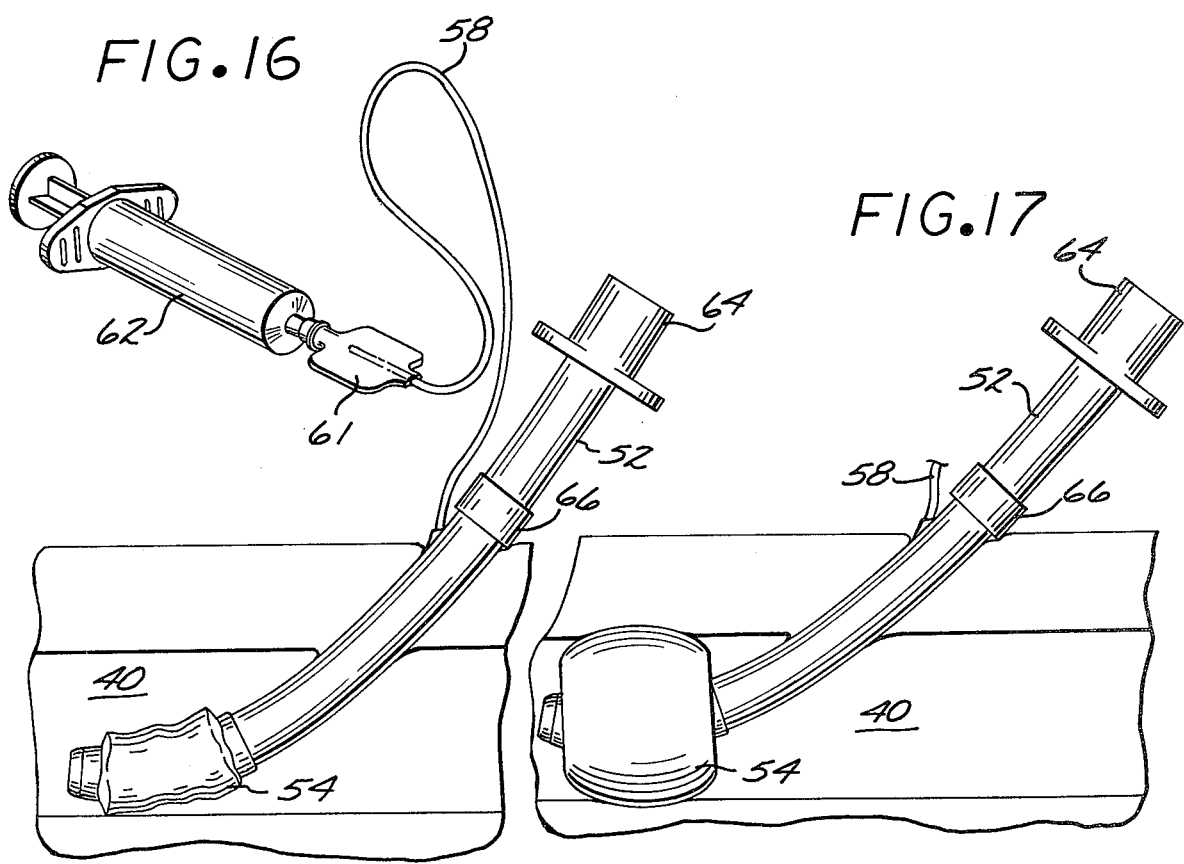

APPARATUS AND METHOD FOR PROVIDING OPENING INTO BODY CAVITY OR VISCUS

CROSS-REFERENCE TO RELATED APPLICATION

This is a continuation-in-part of applicant's co-pending patent application, Ser. No. 206,709, filed Nov. 14, 1980, now U.S. Pat. No. 4,364,391, and entitled "Tracheostomy Apparatus and Method". Related apparatus is also disclosed in my U.S. Pat. No. 3,511,243, issued May 12, 1970 for "Apparatus for Providing a Breathing Conduit Communicating with the Trachea at the Base of the Neck".

BACKGROUND OF THE INVENTION

1. Field of the Invention

The present invention relates to an apparatus and method to perform a percutaneous or non-dissection procedure involving the establishment of an opening or entry into a body cavity or hollow viscus.

2. Description of the Prior Art

A number of devices have been advanced for non-dissection establishment of openings into a body cavity or hollow viscus, notably for tracheostomies. Such devices are normally preferable to dissection procedures, which require considerable surgical skill in that many blood vessels are often involved which tend to bleed profusely during a dissection procedure.

My U.S. Pat. No. 3,511,243 discloses a method and apparatus which utilizes a dilator to which is separably attached a flexible leader. Means are provided for introducing the leader into the tracheal lumen in performing a tracheostomy.

My U.S. patent application, Ser. No. 206,709 discloses a similar method and apparatus, but utilizing a permanently attached dilator leader and an improved means for establishing proper location of elements of the apparatus in the tracheal lumen. The apparatus and method also utilized a pair of co-axially arranged needles to facilitate introduction of the dilator leader into the tracheal lumen, and further utilized a trachea tube in coaxial relation to the dilator for retention in the tracheal lumen upon removal of the dilator. The double needle arrangment was relatively expensive and complex to use, and the coaxial arrangement of the dilator and the trachea tube limited the length of tube which could easily be employed. This was a disadvantage in those instances where the patient's trachea was more deeply located than normal.

SUMMARY OF THE INVENTION

According to the present invention an apparatus and method are provided which utilize a single needle for insertion into the body cavity or hollow viscus. The needle is structurally weakened along a longitudinal line, and includes spreader means operative to split the needle along the structurally weakened line to define an elongated slot. A syringe attached to the needle facilitates insertion of the needle and gives immediate indication of penetration of the body cavity through aspiration, the syringe plunger being readily movable outwardly upon such penetration.

The apparatus includes a dilator insertable through a side opening in a flexible tube, the dilator having a tapered introducer portion coaxial with the distal extremity of the tube.

The distal end of the dilator introducer portion mounts a flexible leader which, after removal of the needle syringe, can be fitted through the bore of the needle. Once the leader is in position, the split needle is separated from the leader and removed. The dilator is forced into the body cavity along the path defined by the leader, carrying the tube with it. The dilator is then removed through the side opening in the tube and a portion of the remaining length of the tube is then thrust into the body cavity.

When the apparatus is used in performing tracheostomies, the flexible tube preferably carries a deflated cuff to which an inflating tube is attached. The cuff is inflated through an associated syringe to block entry into the trachea tube area of any foreign matter from the head and upper throat.

Other objects and features of the invention will become apparent from consideration of the following description taken in connection with the accompanying drawings.

BRIEF DESCRIPTION OF THE DRAWINGS

FIG. 1 is an elevational view of the initial insertion of the needle and syringe of the present apparatus into the tracheal lumen in a tracheostomy procedure, the tracheal lumen being illustrated diagrammatically for simplicity;

FIG. 2 is a view similar to FIG. 1 but illustrating the inclined orientation of the needle subsequent penetration of the trachea;

FIG. 3 is a view smilar to FIG. 2, but illustrating removal of the syringe from the needle;

FIG. 4 is a view similar to FIG. 3, illustrating threading of the dilator leader into the bore of the needle and into the trachea;

FIG. 13 is a view similar to FIG. 12, illustrating the dilator partially withdrawn;

FIG. 14 is a front elevational view of the trachea tube;

FIG. 15 is a transverse cross-sectional view of the trachea tube partially inserted into the trachea;

FIG. 16 is a side elevational view similar to FIG. 15, illustrating attachment of an inflating syringe; and FIG. 17 is a view similar to FIG. 16, illustrating the inflated cuff of the trachea tube.

DESCRIPTION OF THE PREFERRED EMBODIMENTS

As will be seen from the description which follows, the present method and apparatus will be described with reference to tracheostomy procedures. However, with relatively minor and obvious modifications the method and apparatus are equally useful in providing an opening or entry into any other body cavity or hollow viscus, such as in a thocostomy to provide an opening into the thorax, a peritonoscopy to provide an opening into the abdominal cavity, or a cystostomy to provide an opening into the bladder. Accordingly, the specific reference hereinafter to tracheostomies is merely exemplary.

The present apparatus and method are, like the apparatus of my co-pending patent application Ser. No. 206,709, adapted to be employed to perform a percutaneous tracheostomy, in contrast to a dissection tracheostomy which involves extensive surgical cutting of tissues and attendant skill. The present apparatus and method do not require the same level of skill and are therefore adapted for use in emergency situations by persons not having extensive surgical training.

In performing a tracheostomy, the initial steps of the present method utilize a single needle in association with a syringe. The syringe plunger can be withdrawn when the needle is located within the tracheal lumen, a knowledge of such location being critical to a successful tracheostomy. An important feature of the present method and apparatus is the employment of a unique form of needle which is structurally weakened in such a way that it can be split open to provide a slot. As will be seen, the needle bore provides a path for insertion of a flexible leader into the tracheal lumen. Splitting of the needle provides a slot through which the needle can be laterally separated for withdrawal of the needle from the trachea. The leader is attached to a dilator which is thereafter pressed inwardly to progressively enlarge or expand the needle opening occupied by the leader, followed by placement of a breathing or trachea tube associated with the dilator. The tube provides a breathing passageway.

As will be apparent to those skilled in the medical arts, the various components of the present apparatus are configured and dimensioned to suit the size and condition of the patient, the dimensions being made smaller in the case of children, for example. In addition, it is an important feature of the present invention that the trachea tube utilized can be inserted far enough to reach the deeply located trachea characteristic of some individuals.

The figures of the drawings generally follow the sequence of steps which characterize practice of the present method.

Figure 6:
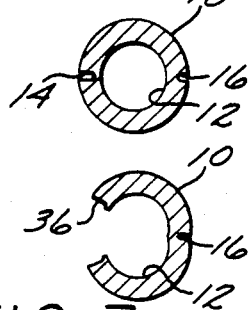
FIG. 6 is an enlarged view taken along the line 6—6 of FIG. 4 prior to splitting open of the needle.

With reference to FIG. 1, the present apparatus comprises an elongated needle 10 having a wedge-shaped distal end to facilitate penetration of the trachea and associated tissue and cartilage. The needle inclues a central bore 12 and is structurally weakened longitudinally by provision of a very small groove 14, as seen in FIG. 6, which extends almost completely through the thickness of the wall of the needle 10. Preferably the needle 10 is also structurally weakened, but to a lesser extent, by a longitudinal groove 16 located oppositely of the groove 14.

Figure 5:
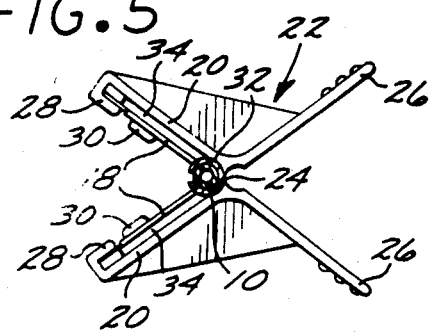
FIG. 5 is a view taken along the line 5—5 of FIG. 4.
Figure 8:
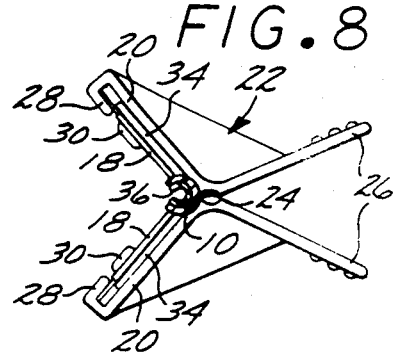
FIG. 8 is a view similar to FIG. 5, illustrating the position of the spreader components subsequent to splitting open of the needle.
Figure 7:
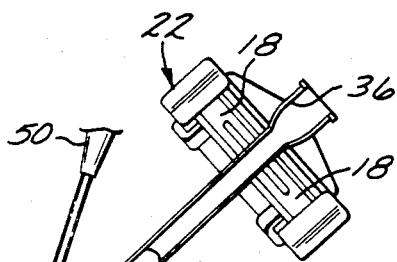
FIG. 7 is a view similar to FIG. 6, illustrating the split open needle.
Figure 9:
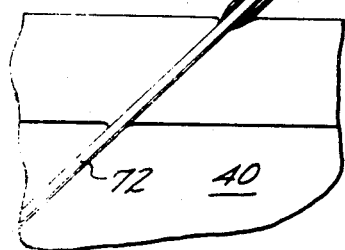
FIG. 9 is a view similar to FIG. 4, illustrating lateral separation of the leader from the split open slot of the needle during withdrawal of the needle.

A pair of metal spreader tabs 18 are spot welded or otherwise rigidly affixed at their ends to the needle 10 on opposite sides of the groove 14, as best seen in FIGS. 5 and 8. If desired, the tabs 18 could be a single length of metal extending around the needle 10 in overlying relation to the groove 16.

Although to be seen in the drawings, the needle adjacent the grooves 14 and 16 is provided with a suitable polymer or other coating to prevent leakage of air through the grooves to the needle bore 12.

A needle of the type described is presently available on the market for intravenous feeding and the like. It is believed that the grooves 14 and 16 are precision formed by laser beam techniques. In this application the tabs 18 are grasped between the thumbs and forefingers of each hand and are spread apart to split open the groove 14 to the bore 12 and define a slot. The groove 16 normally does not split through to the bore 12, serving instead as a form of hinge. The slot thus defined enables the associated catheter to pass through the slot for retention in the vein as the needle is removed.

In the present invention this form of needle has been modified to enable splitting open of the needle 10 in a one-handed procedure. More particularly, a fitting or spreader 22 is made of plastic material such as polyethylene in an X-shape configuration, the upper portion of the spreader 22 being defined by upwardly divergent legs 20 whose inner extremities are joined and extend around the corresponding inner extremities of the tabs 18, the juncture of the legs 20 defining a hinge 24. The lower portion of the X-shape configuration of the spreader 22 is defined by a pair of downwardly divergent legs 26 integral with the legs 20.

The tabs 18 rest upon the inner faces of the upper legs 20, and the outer ends of the tabs 18 fit under and are held in position by a pair of end flanges 28 integral with the upper legs 20. The distal side edges of the tabs 18 underlie and are held in position by a pair of side flanges 30 also integral with the upper legs 20.

A cylindrical syringe receiver 32 having upwardly divergent wings or tabs 34 is located adjacent the proximal end of the needle 10. The tabs 34 are held between the legs 20 and the tabs 18. The central portion of the syringe receiver 32 constitutes an extension of the bore of the needle 10 and it is split along a line in alignment with the needle groove 14.

With the foregoing arrangement, the needle 10 can be spread open or split along the groove 14 by grasping the opposite legs 26 between the thumb and forefinger of one hand and urging them apart. Such a one-handed procedure leaves the other hand free to manipulate the dilator leader, as will be seen.

In practicing the present method and apparatus, the needle 10 is detachably fitted at the syringe receiver 32 to a usual and conventional syringe 38. As seen in FIG. 1, the needle 10 is inserted into the area adjacent the tracheal lumen, its location within the tracheal lumen 40 being signalled by the ability of the physician to withdraw the syringe plunger 41 by withdrawing air from the trachea. At this time no air can enter through the grooves 14 or 16 because of the fluid tight coating on the needle 10.

Once the needle 10 has entered the trachea, it is angled at approximately 45 degrees in a direction down the throat, as illustrated in FIG. 2, the needle 10 next being advanced approximately 6 to 8 millimeters. The syringe 38 is then removed from the syringe receiver 32, as seen in FIG. 3.

An elongated dilator 44 is next employed to enlarge the opening for the trachea tube an introduce a leader for the trachea breathing tube. The dilator 44 includes an elongated handle portion 46 integral with a curved or arcuate intermediate portion 48 which terminates in a downwardly tapering conical introducer portion 50. The larger diameter of the introducer portion 50 is the same as that of the intermediate portion 48.

The distal end of the introducer portion 50 mounts an elongated flexible leader 72 made of any suitable flexible material, such as a thin tube of polyethylene. The leader 72 and distal end of the introducer portion 48 are inserted within a cut or incision defining a side opening in the trachea tube 52.

The trachea tube 52 is conveniently made of a length of plastic surgical tubing which is rounded at its distal end to facilitate movement along the tracheal lumen. The plastic material is flexible enough for the side opening to spread and receive the dilator 44, and also sufficiently resilient to substantially close the side opening upon removal of the dilator.

The tube 52 is coaxial at its distal extremity with the distal portion of the curved intermediate portion 50 of the dilator 44, as seen in FIG. 4.

Although not necessary in procedures other than tracheostomies, the tube 52 mounts a plastic cuff 54 at its lower or distal extremity. The cuff 54 has an inflatable central portion an is adhered at its opposite extremities to the outer surface of the trachea tube 52. As best seen in FIG. 15, an opening 56 is formed in the wall of the trachea tube 52 to provide communication between the interior of the cuff 54 and the distal end of an air tube 58. The tube 58 extends toward the proximal extremity of the trachea tube 52 and through a suitable opening 60 provided in the side of the trachea tube 52 for communication with the interior of an air bag 61. The air bag 61 is press fitted over the end of an air inflating syringe 62 for a purpose which will subsequently be described.

At the opposite or proximal extremity of the tube 52 a respirator fitting 64 is press fitted within the tube, and a stop collar 66 is fitted about and adhered to the outside of the tube 52 to prevent any possible passage of the tube 52 into the trachea if the respirator fitting 64 were removed.

A blade or cutting edge 68 mounted in a recess 70 formed in the intermediate portion 48 is adapted to cut tissues which are forceably stretched across it upon introduction of the dilator 44 into the tracheal lumen, as will be seen.

The flexible nature of the leader 72 enables it to be easily threaded into the open upper end of the bore 12 of the needle 10 for projection into the tracheal lumen, as seen in FIG. 4. The leader 72 tends to align itself with the trachea for later guiding of the dilator 44.

Once the leader 72 is inserted to the extend illustrated in FIG. 4, the needle 10 is split open along the groove 14 and the leader 72 is laterally separated from the needle 10 during withdrawal of the needle. The split open groove 14 through which the leader is laterally separated is maintained open by steady pressure upon the spreader legs 26.

Figure 10:
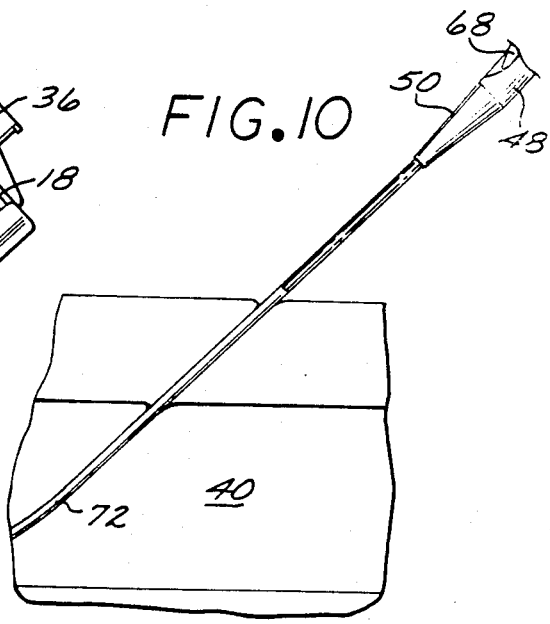
FIG. 10 is a view similar to FIG. 9, illustrating the dilator orientation prior to its penetration of the trachea.

The axis of the dilator introducer portion 48 is next oriented at approximately a 45 degree angle, as seen in FIG. 10, and forced into the opening through which the leader 72 extends. The tissues are forced apart by the tapered introducer portion 50 and by the larger diameter trachea tube 52 which follows it. The flexible cuff 54 conforms itself to the opening and easily slides through. This dilating rather than cutting action minimizes bleeding and provides a desired tamponade effect. The only cutting of the tissues is that which is necessary to relieve the tension of tissues froceably stretched across the intermediate portion and into contact with the blade 68.

The dilator 30 is next withdrawn from the trachea, being extracted through the side opening in the trachea tube 52, the side opening tending to close because of the resilience or "memory" of the plastic material of which the tube 52 is made. The tube 52 is left in position, as seen in FIG. 15, and can be thrust further into the trachea if the trachea is deeply located, as is the case in certain patents.

Figure 11:
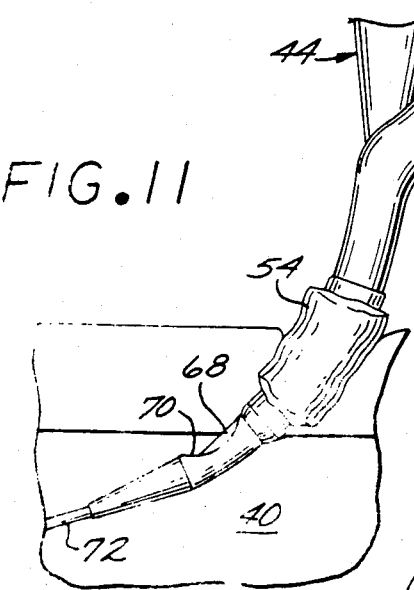
FIG. 11 illustrates initial penetration of the trachea by the dilator and trachea tube.
Figure 12:
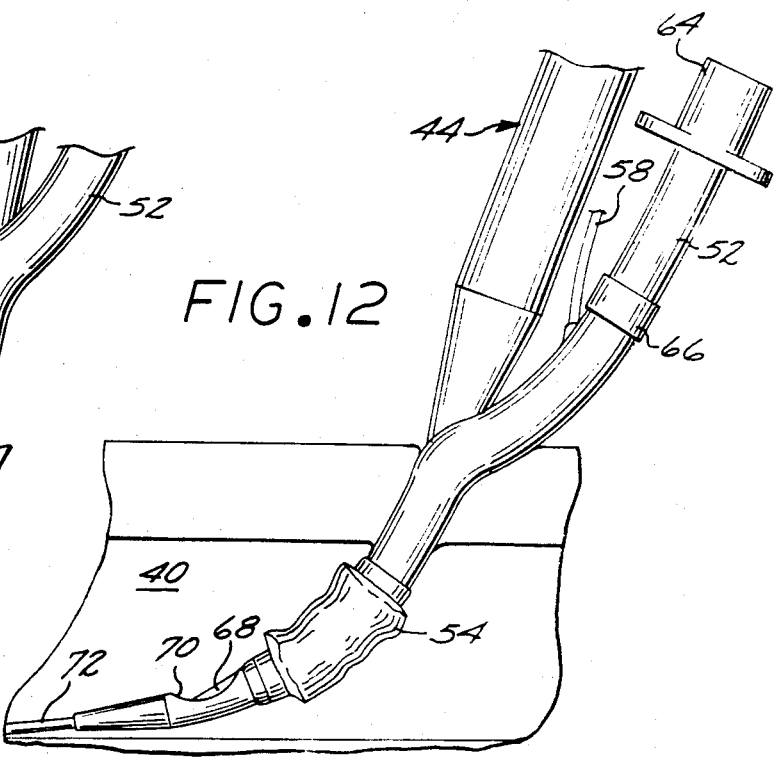
FIG. 12 is a view similar to FIG. 11, illustrating a more complete insertion of the trachea tube.

The thin cuff 54 is collapsed closely upon the tube 52 during insertion of the tube into the trachea, as seen in FIGS. 11-13. After insertion the cuff 54 can be inflated by depressing the plunger of the syringe 62. The inflated cuff 54 blocks the throat upwardly of the open distal end of the trachea tube 52, as seen in FIG. 17. A respirator (not shown) can now be attached to the respirator fitting 64 and operated in the usual fashion, as will be obvious to those skilled in the art.

From the foregoing it will apparent that the single needle 10 significantly simplifies the insertion procedure, and the arrangement enabling the dilator 44 to be introduced into the side of the trachea tube 52 permits use of a longer trachea tube, in the order of 25 millimeters longer than that which could be employed in the apparatus of my pending application, Ser. No. 206,709.

Various modifications and changes may be made with regard to the foregoing detailed description without departing from the spirit of the invention, particularly with respect to procedures other than tracheostomies.

I claim:

1. An apparatus for performing a percutaneous procedure to provide an opening or entry into a body cavity or hollow viscus, and which includes a flexible tube, a dilator for fitting through said tube, and an elongated flexible leader on said dilator adapted for insertion through the bore of a needle whereby, upon insertion of the needle into the body cavity or hollow viscus said leader provides a path for insertion of said dilator and said tube into the body cavity or hollow viscus, an improved needle means for receiving said leader in the bore thereof, said needle means comprising:

an elongated hollow needle having a sharpened distal extremity, a proximal extremity having an open end for introduction of said leader, and a structurally weakened area extending longitudinally between said distal and proximal extremities; and spreader means fixed to said needle and comprising tab means having upwardly divergent legs projecting from opposite sides of said area adjacent said proximal extremity, and further comprising a spreader receiving and holding said legs and including downwardly divergent legs movable toward each other to spread apart said upwardly divergent legs to pull apart the wall of said needle in said area adjacent said proximal extremity to define a groove and to propagate said groove to said distal extremity whereby said leader may be laterally separated from said needle for withdrawal of said needle for withdrawal of said needle means prior to said insertion of said dilator and said trachea tube.

2. A percutaneous non-dissection method for providing an opening or entry into a body cavity or hollow viscus, said method comprising the steps of:

forming an entry to the body cavity or hollow viscus by insertion of a needle having means forming or adapted to form a longitudinal slot along its length;

locating adjacent said needle a rigid dilator having an arcuate portion mounting a flexible leader, said arcuate portion projecting through the side and out the distal end of a flexible breathing tube;

threading said flexible leader through the central bore of said needle until said leader enters the body cavity or hollow viscus;

laterally separating said leader from said needle through said longitudinal slot while withdrawing said needle;

inserting said dilator and tube into the body cavity or hollow viscus along the opening defined by said leader; and withdrawing said dilator and said leader from said body opening or hollow viscus and from said tube, leaving the distal extremity of said tube in said body opening or hollow viscus, and with the proximal extremity of said tube projecting a predetermined distance outwardly of said entry.

3. The method of claim 1 wherein said tube is relatively long, and the step of urging a portion of said projecting proximal extremity of said tube farther into the body opening or hollow viscus.

4. Apparatus for performing a percutaneous non-dissection procedure to provide an opening or entry into a body cavity or hollow viscus, said apparatus comprising:

a flexible tube open at its distal and proximal ends and including a side opening and further including stop means located adjacent said proximal end a predetermined distance from said side opening;

an elongated dilator having an arcuate portion adapted to fit through said side opening and project through said distal end of said tube, said dilator mounting at its distal end an elongated flexible leader adapted for insertion through the bore of a needle, said dilator being rigid relative to said tube to facilitate entry through said side opening; and a needle for insertion into the body cavity or hollow viscus and adpated to receive said leader, said needle having means for defining a longitudinal slot whereby said needle may be removed from the body cavity or hollow viscus to leave said leader in place, said leader thereby providing a path for insertion of said dilator and said tube into the body cavity or hollow viscus, and said dilator being slidably removable from said side opening for separation from said tube to leave said tube in place in said body cavity or hollow viscus with said proximal end projecting outwardly of said entry whereby said tube may be urged said predetermined distance farther into said body cavity or hollow viscus.

5. Apparatus according to claim 4 wherein said side opening is an incision spreadable to receive said dilator, said tube being made of a plastic material tending to close said incision upon removal of said dilator from said incision.

6. Apparatus according to claim 4 wherein said means defining said longitudinal slot comprises a structurally weakened area extending longitudinally between the distal and proximal extremities of said needle, and said needle includes spreader means operative to cause failure of said structurally weakened area and formation of said longitudinal slot.

7. Apparatus according to claim 6 and including a fluid-tight coating overlying said structurally weakened area.

* * * * *